(12) United States Patent
Mejia

(10) Patent No.: US 7,027,851 B2
(45) Date of Patent: Apr. 11, 2006

(54) MULTI-TIP STEERABLE CATHETER

(75) Inventor: Ruth N. Mejia, West Covina, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 268 days.

(21) Appl. No.: 10/671,101

(22) Filed: Sep. 25, 2003

(65) Prior Publication Data

US 2004/0087848 A1    May 6, 2004

Related U.S. Application Data

(60) Provisional application No. 60/422,227, filed on Oct. 30, 2002.

(51) Int. Cl.
*A61B 5/04*    (2006.01)
(52) U.S. Cl. .................................... 600/374
(58) Field of Classification Search ................ 600/374, 600/381; 606/41; 607/122
See application file for complete search history.

(56) References Cited

U.S. PATENT DOCUMENTS 5,237,996 A     8/1993   Waldman et al.
5,327,889 A  *  7/1994   Imran ........................ 600/374

(Continued)

OTHER PUBLICATIONS

International Search Report dated Mar. 18, 2004 from European Application No. EP03256844.6

*Primary Examiner*—Lee S. Cohen
(74) *Attorney, Agent, or Firm*—Christie, Parker & Hale, LLP

(57) ABSTRACT

An improved catheter is provided that is particularly useful for simultaneously mapping electrical activity at multiple locations within the heart. The catheter comprises an elongated catheter body having proximal and distal ends and at least one lumen extending longitudinally therethrough. A control handle is attached to the proximal end of the catheter body. A mapping assembly is mounted to the distal end of the catheter body. The mapping assembly comprises at least two elongated flexible spines, each spine having a proximal end attached to the distal end of the catheter body and a free distal end. Each spine carries at least one electrode along its length. The catheter further comprises at least two spine puller wires, each spine puller wire corresponding to one of the at least two spines. Each spine puller wire has a proximal end anchored in the handle and a distal end anchored at or near the distal end of its corresponding spine such that, in use, longitudinal movement of a spine puller wire relative to the catheter body results in deflection of the spine in which the spine puller wire is anchored. The use of a plurality of spines permits simultaneous mapping of multiple points, increasing the speed of mapping of regions of interest.

13 Claims, 3 Drawing Sheets

U.S. PATENT DOCUMENTS

| | | |
|---|---|---|
| 5,551,426 A | 9/1996 | Hummel et al. |
| 5,702,438 A | 12/1997 | Avitall |
| 5,728,143 A | 3/1998 | Gough et al. |
| 5,855,576 A | 1/1999 | LeVeen et al. |
| 5,935,102 A | 8/1999 | Bowden et al. |
| 5,951,547 A | 9/1999 | Gough et al. |
| 6,068,629 A | 5/2000 | Haissaguerre et al. |
| 6,071,280 A | 6/2000 | Edwards et al. |
| 6,231,570 B1 | 5/2001 | Tu et al. |
| 6,237,605 B1 | 5/2001 | Vaska et al. |
| 6,374,476 B1 | 4/2002 | Ponzi et al. |
| 6,402,746 B1 | 6/2002 | Whayne et al. |
| 6,638,277 B1 * | 10/2003 | Schaefer et al. ............ 606/41 |
| 2001/0001819 A1 | 5/2001 | Lee et al. |
| 2002/0087157 A1 | 7/2002 | Sliwa, Jr. et al. |
| 2003/0050637 A1 | 3/2003 | Maguire et al. |

* cited by examiner

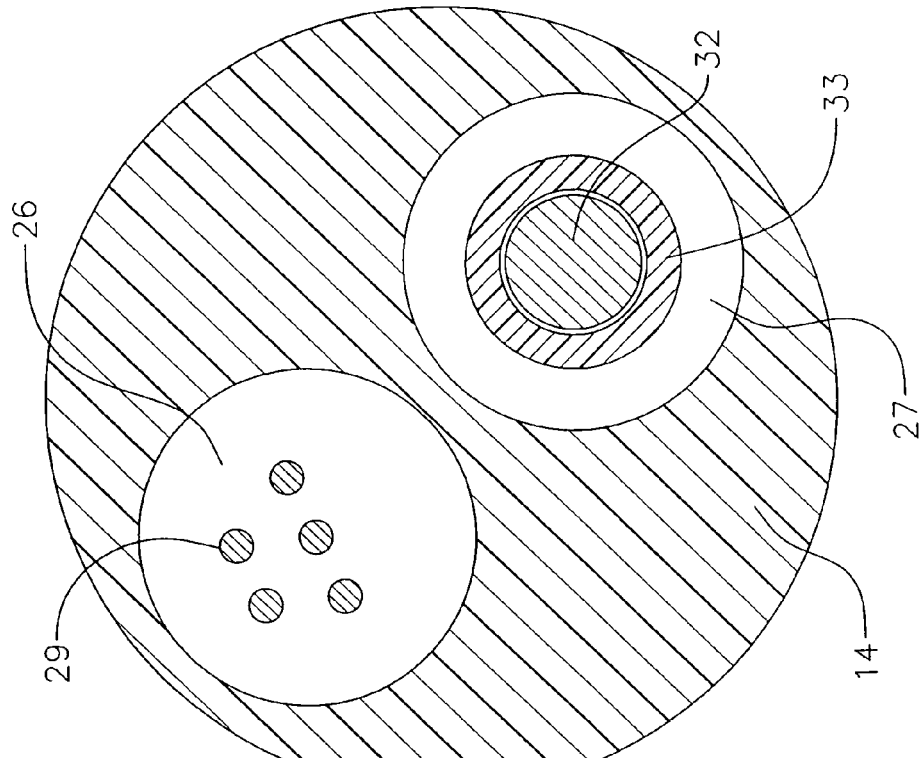
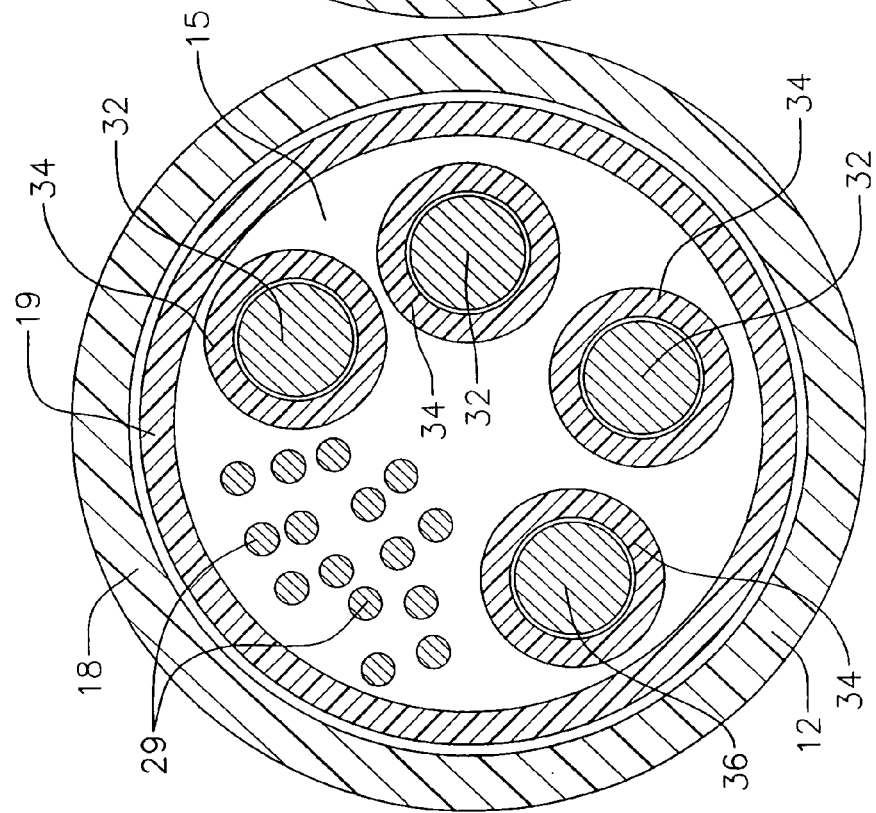

MULTI-TIP STEERABLE CATHETER

CROSS-REFERENCE TO RELATED APPLICATION

This application claims the benefit of U.S. Provisional Application No. 60/422,227, filed Oct. 30, 2002, the entire disclosure of which is incorporated herein by reference.

BACKGROUND OF THE INVENTION

Electrophysiology catheters are commonly used for mapping electrical activity in a heart. By mapping the electrical activity in the heart, one can detect ectopic sites of electrical activation or other electrical activation pathways that contribute to heart malfunctions. This type of information may then allow a cardiologist to intervene and destroy the malfunctioning heart tissues. Such destruction of heart tissue is referred to as ablation, which is a rapidly growing field within electrophysiology and obviates the need for maximally invasive open heart surgery.

Such electrophysiology mapping catheters typically have an elongated flexible body with a distal end that carries one or more electrodes that are used to map or collect electrical information about the electrical activity in the heart. The distal end can be steerable or deflectable to assist the user in properly positioning the catheter for mapping in a desired location. However, often numerous electrical measurements must be taken to properly map the heart, which can be time consuming if the measurements are taken one at a time. Accordingly, a need exists for an improved catheter that can take multiple measurements simultaneously to make the mapping process more efficient.

SUMMARY OF THE INVENTION

The present invention is directed to an improved catheter for mapping the electrical activity in a heart. The catheter comprises a plurality of deflectable spines, each capable of obtaining electrical, mechanical and/or locational data. The use of a plurality of spines permits simultaneous mapping of multiple points, increasing the speed of mapping of regions of interest, e.g., the left and right ventricles.

In one embodiment, the invention is directed to a catheter comprising an elongated catheter body having a proximal end, a distal end and at least one lumen extending longitudinally therethrough. A control handle is attached to the proximal end of the catheter body. A mapping assembly is mounted at the distal end of the catheter body. The mapping assembly comprises at least two elongated flexible spines, each spine having a proximal end fixedly attached at or near the distal end of the catheter body and a free distal end. Each spine carries at least one electrode along its length. The catheter further comprises at least two spine puller wires, each spine puller wire corresponding to one of the at least two spines. Each spine puller wire has a proximal end anchored in the handle and a distal end anchored at or near the distal end of its corresponding spine such that, in use, longitudinal movement of a spine puller wire relative to the catheter body results in deflection of the spine in which the spine puller wire is anchored.

DESCRIPTION OF THE DRAWINGS

These and other features and advantages of the present invention will be better understood by reference to the following detailed description when considered in conjunction with the accompanying drawings wherein:

FIG. 2 is an end cross-sectional view of the catheter body of FIG. 1 taken along line 2—2.

FIG. 3 is an end cross-sectional view of a spine of the catheter of FIG. 1 taken along line 3—3.

DETAILED DESCRIPTION OF THE INVENTION

The invention is directed to a catheter having at its distal end a mapping assembly comprising a plurality of steerable or deflectable spines. Each spine carries one or more electrodes such that, when the spines are positioned in contact with heart tissue, each spine is capable of obtaining electrical data.

Figure 1:
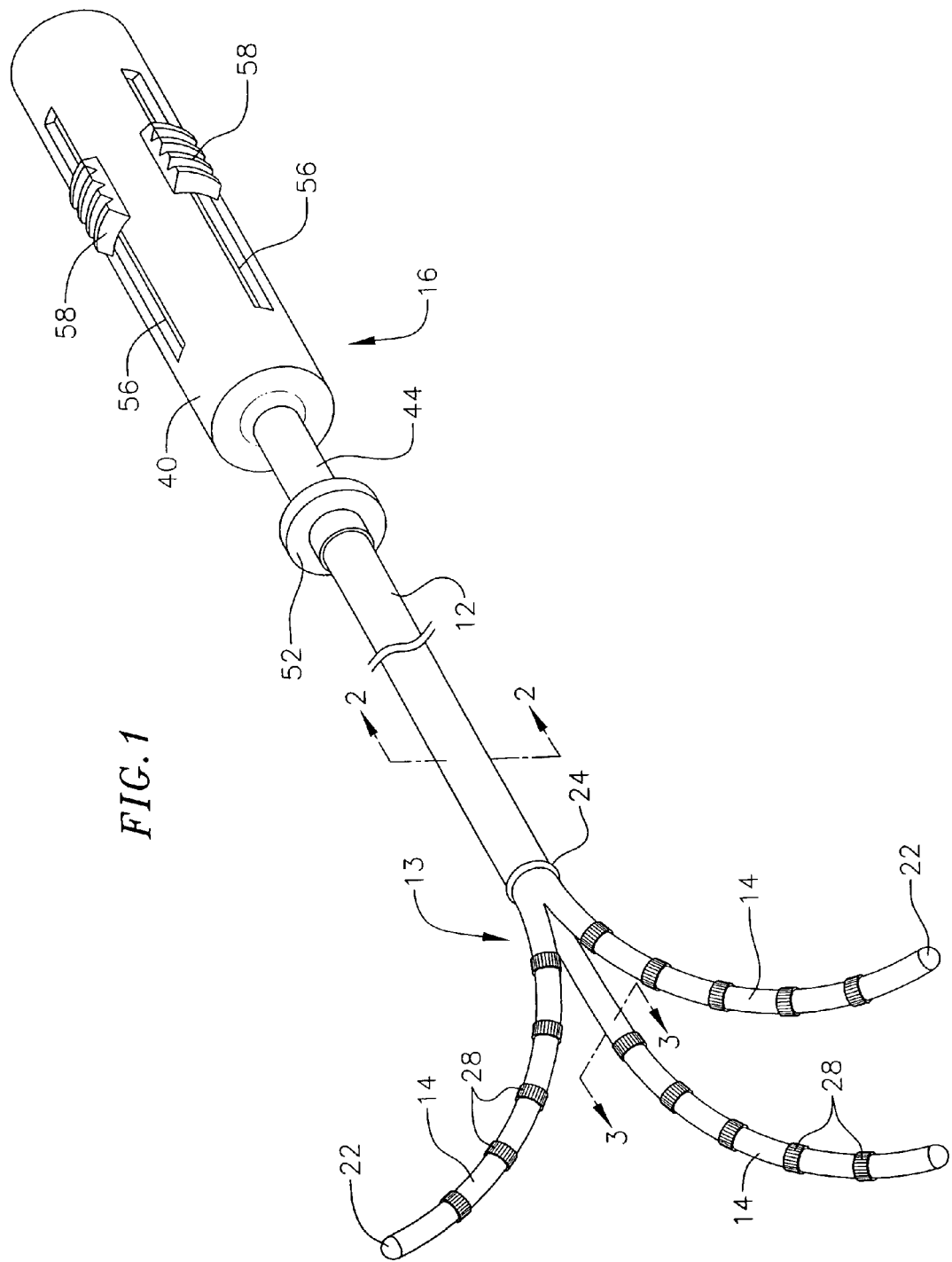
FIG. 1 is a perspective view of a catheter according to the invention.

As shown in FIG. 1, the catheter comprises an elongated catheter body 12 having proximal and distal ends, a mapping assembly 13 comprising a plurality of spines 14 mounted at the distal end of the catheter body, and a control handle 16 at the proximal end of the catheter body.

As shown in FIGS. 1 and 2, the catheter body 12 comprises an elongated tubular construction having a single, axial or central lumen 15, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 18 made of polyurethane or PEBAX® (polyether block amide). The outer wall 18 preferably comprises an imbedded braided mesh of stainless steel or the like, as is generally known in the art, to increase torsional stiffness of the catheter body 12 so that, when the control handle 16 is rotated, the distal end of the catheter body 12 will rotate in a corresponding manner.

A stiffening sleeve 19 is coaxially mounted in the lumen 15 of the catheter body 12 to provide improved torsional stability. The stiffening sleeve 19 preferably has an outer diameter that is slightly smaller than the inner diameter of the outer wall 18. The stiffening sleeve 19 is preferably made of polyimide or other suitable biocompatible plastic. If desired, the stiffening sleeve can be eliminated.

The length of the catheter body 12 is not critical, but preferably ranges from about 90 cm to about 120 cm, and more preferably is about 110 cm. The outer diameter of the catheter body 12 is also not critical, but is preferably no more than about 8 french, more preferably about 7 french. Likewise, the thickness of the outer wall 18 is not critical, but is preferably thin enough so that the central lumen 15 can accommodate all necessary wires and other components extending through the catheter body 12.

In the depicted embodiment, the mapping assembly 13 comprises three spines 14. As will become apparent, the number of spines can vary as desired, and preferably ranges from two to twelve, more preferably from three to eight. Each spine 14 has a proximal end attached at the distal end of the catheter body 12 and a free distal end, i.e., the distal end is not attached to any of the other spines, to the catheter body, or to any other external structure that confines movement of the distal end. Each spine 14 comprises a plastic tubing made of any suitable biocompatible material, such as PEBAX or polyurethane, having one or more lumens extending therethrough. Preferably each spine 14 comprises a multi-lumen, more preferably a dual-lumen, extrusion. In the depicted embodiment, each spine includes a lead wire lumen 26 and a puller wire lumen 27, discussed further below. The puller wire lumen 27 is preferably off-axis. As would be recognized by one skilled in the art, the number, sizes and arrangement of the lumens can vary as desired. The lengths the spines will depend on the particular application for which the catheter is being used. Preferably each spine has a length ranging from about 0.5 cm to about 25 cm, more preferably from about 1 cm to about 10 cm, still more preferably from about 2 cm to about 7 cm.

If desired, each spine 14 can have a preformed shape. This can be accomplished by including in each spine 14 a support arm (not shown)comprising a metal or plastic material that has shape memory, such as nitinol, so that the support arm forms an initial shape when no external forces are applied, forms a deflected shape when an external force is applied, and returns to its initial shape when the external force is released. Such a design is disclosed in U.S. patent application Ser. No. 10/231,875, entitled "Catheter and Method for Mapping Purkinje Fibers," the entire disclosure of which is incorporated herein by reference.

The spines 14 are connected to each other and to the distal end of the catheter body 12 at their proximal ends, as shown in FIG. 1. Preferably the proximal ends of the spines 14 are melted, glued or otherwise fused to each other and to the distal end of the catheter body 12 at a junction 24 to provided a unitary construction. Thus the spines 14 are permanently attached to the catheter body 12 and not retractable into the catheter body.

In the depicted embodiment, the distal end of each spine 14 has an atraumatic tip comprising a polyurethane cap 22. Each polyurethane cap is glued or otherwise fixedly attached to the distal end of its corresponding spine 14. Other atraumatic tip designs could be used in connection with the invention.

As described in more detail below, the spines 14 are moveable between a deflected arrangement, wherein, for example, each spine extends outwardly from the catheter body 12, or the spines 14 may be arranged in a collapsed arrangement, wherein, for example, each spine is disposed generally parallel to the longitudinal axis of the catheter body 12 so that the spines are capable of fitting within a lumen of a guiding sheath, as discussed further below.

Each spine 14 carries at least one electrode mounted along its length. In the depicted embodiment, five ring electrodes 28 are mounted, preferably evenly-spaced, on each spine 14. As would be recognized by one skilled in the art, the number and arrangement of the electrodes on each spine can vary as desired. For example, one or more of the spines 14 could carry a tip electrode (not shown) on the distal end of the spine in place of the polyurethane cap 22. Each ring electrode 28 has a length preferably up to about 2 mm, more preferably from about 0.5 mm to about 1 mm. The distance between the ring electrodes 28 preferably ranges from about 1 mm to about 10 mm, more preferably from about 2 mm to about 5 mm. Preferably each spine carries from 2 to about 20 electrodes, more preferably from 3 to 10 electrode.

Each ring electrode 28 is electrically connected to an electrode lead wire 29, which in turn is electrically connected to a connector 17 at the proximal end of the catheter. The connector 17 is connected to an appropriate mapping or monitoring system (not shown). Each electrode lead wire 29 extends from the connector 17, through the control handle 16, through the central lumen 15 in the catheter body 12, and into the lead wire lumen 26 of the spine 14 where it is attached to its corresponding ring electrode 28. Each lead wire 29, which includes a non-conductive coating over almost all of its length, is attached to its corresponding ring electrode 28 by any suitable method.

A preferred method for attaching a lead wire 29 to a ring electrode 28 involves first making a small hole through the wall of the spine 14. Such a hole can be created, for example, by inserting a needle through the wall of the spine 14 and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 may be formed by wrapping the lead wire 29 around the spine 14 a number of times and stripping the lead wire of its own non-conductive coating on its outwardly facing surfaces. In such an instance, the lead wire 29 functions as a ring electrode.

Additionally, a mechanism is provided for individually deflecting or steering each of the spines 14. Specifically, a spine puller wire 32 is provided for each spine 14. Each spine puller wire 32 has a proximal end anchored to the control handle 16, as described further below, and a distal end anchored at or near the distal end of its corresponding spine 14. Each spine puller wire 32 extends through the puller wire lumen 27 of its corresponding spine and through the central lumen 15 of the catheter body 12. Each spine puller wire 32 is made of any suitable metal, such as stainless steel or Nitinol, and is preferably coated with Teflon® or the like to impart lubricity to the puller wire. Each puller wire 32 preferably has a diameter ranging from about 0.006 to about 0.010 inches. Within each spine 14, a plastic, preferably Teflon®, protective sleeve 33 is provided in surrounding relation to each puller wire 32 to prevent the puller wire from cutting through the wall of the spine during deflection.

A preferred mechanism for anchoring a spine puller wire 32 to its corresponding spine 14 comprises a T-bar anchor, as generally described in U.S. Pat. Nos. 5,893,885 and 6,066,125, the entire disclosures of which are incorporated herein by reference. If a spine 14 carries a tip electrode, the spine puller wire 32 can be anchored in the tip electrode, as also described in U.S. Pat. No. 6,066,125. Alternatively, a spine puller wire 32 can be attached to the side of the spine 14, as generally described in U.S. Pat. No. 6,123,699, the entire disclosure of which is incorporated herein by reference. Other arrangements for anchoring a spine puller wire to the distal end of a spine are included within the scope of the invention.

A compression coil 34 is situated within the catheter body 12 in surrounding relation to each spine puller wire 32. Each compression coil 34 extends from the proximal end of the catheter body 12 to the junction 24 of the catheter body and mapping assembly 13. Each compression coil 34 is made of any suitable metal, preferably stainless steel. Each compression coil 34 is tightly wound on itself to provide flexibility, i.e., bending, but to resist compression. The inner diameter of each compression coil 34 is preferably slightly larger than the diameter of its corresponding spine puller wire 32. The Teflon® coatings on the puller wires 32 allows them to slide freely within the compression coils 34. If desired, the outer surface of each compression coil 34 can be covered by a flexible, non-conductive sheath (not shown), e.g., made of polyimide tubing, to prevent contact between the compression coil 34 and the lead wires 29 within the catheter body 12.

A catheter puller wire 36 can also be provided for deflection of the distal end of the catheter body 12 near the junction 24 of the catheter body and mapping assembly 13. With such a design, the catheter puller wire 36 is anchored at its distal end to the outer wall 13 of the catheter body near the junction 24, as generally described in U.S. Pat. No. 6,123,699, and is anchored at its proximal end to the control handle 16, as discussed further below. Within the catheter body 12, the catheter puller wire 36, like the spine puller wires 32, extends through a compression coil 34. If desired, the distal end of the catheter body 12 can comprise a piece of tubing (not shown) that is more flexible than the rest of the catheter body and that contains an off-axis lumen (not shown) into which the distal end of the catheter puller wire 36 extends, as generally described in U.S. Pat. No. 6,123, 699.

Longitudinal movement of a spine puller wire 32 relative to the catheter body 12, which results in deflection of the corresponding spine 14, is accomplished by suitable manipulation of the control handle 16. Similarly, longitudinal movement of the catheter puller wire 36 relative to the catheter body 12, which results in deflection of the distal end of the catheter body proximal to the mapping assembly 13, is accomplished by suitable manipulation of the control handle.

Figure 4:
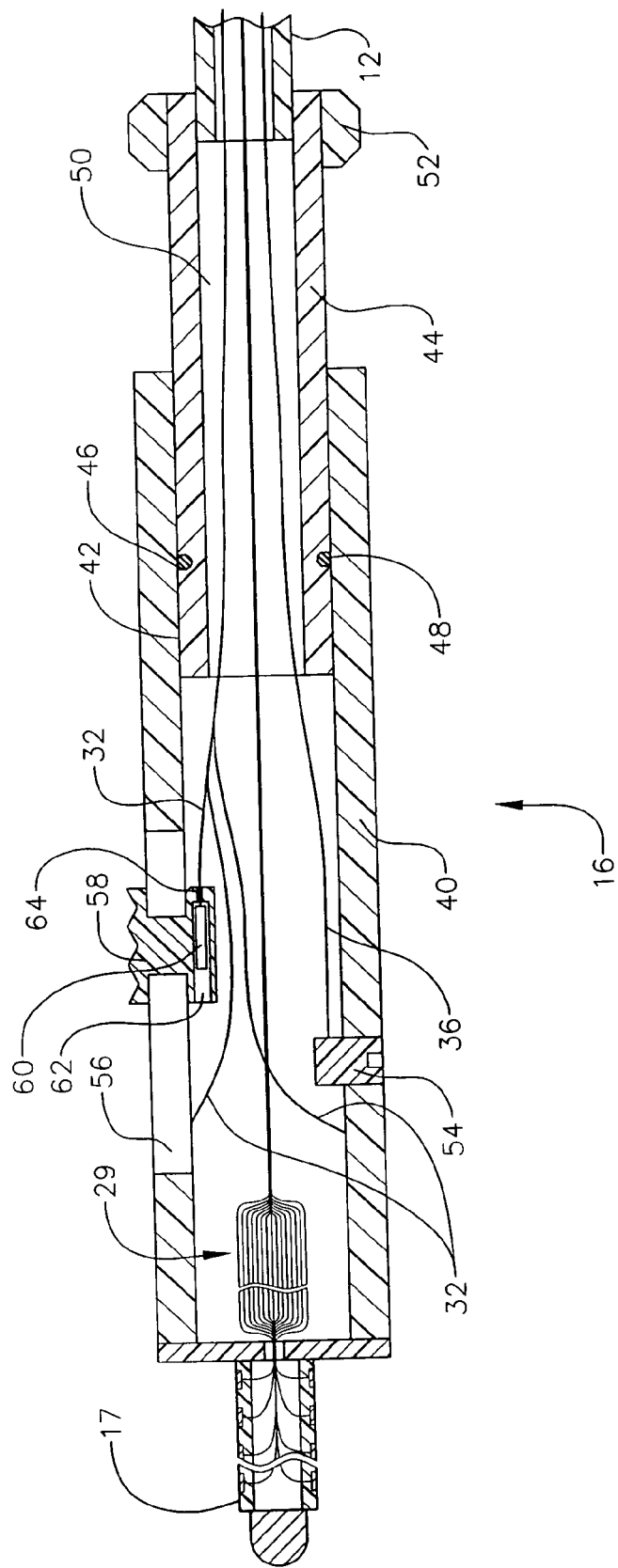
FIG. 4 is a side cross-sectional view of the control handle of the catheter of FIG. 1.

As shown in FIGS. 1 and 4, a preferred control handle comprises a generally cylindrical housing 40 having a piston chamber 42 at its distal end. A generally cylindrical piston 44 is disposed within and generally coaxial with the piston chamber 42. The piston 44 includes a circumferential O-ring notch 46 that carries an O-ring 48 to provide a snug, watertight fit between the piston and the wall of the piston chamber 42. The piston 44 has an axial bore 50 along its length. The diameter of the axial bore 50 is approximately the same as the outer diameter of the catheter body 12. The proximal end of the catheter body 12 extends into the axial bore 50 and is fixedly attached, for example, by glue, to the piston 44. The spine puller wires 32, catheter puller wire 36, and electrode lead wires 29 extend from the catheter body 12, through the axial bore 50 of the piston 44 and into the control handle 16.

The distal end of the piston 44 extends beyond the distal end of the housing 40 so that it can be manually controlled by the user. An annular thumb control 52 is attached at or near the distal end of the piston 44 to facilitate lengthwise movement of the piston relative to the housing 40.

The proximal end of the catheter puller wire 36 is anchored to the housing 40 by any suitable method. In the depicted embodiment, the catheter puller wire 36 is anchored to the housing by means of an anchor 54 that extends into a transverse hole in the housing proximal to the piston chamber 42. Such a design is described in more detail in U.S. Pat. No. 5,383,923, the entire disclosure of which is incorporated herein by reference. In use, the distal end of the catheter body 12 can be curved or bent by moving the piston 44 distally out of the piston chamber 42 by pushing outwardly on the thumb control 52.

For longitudinal movement of the spine puller wires 32, the housing includes three longitudinal slots 56, preferably generally evenly-spaced about its circumference. A slider 58 is slidably mounted in each longitudinal slot 56, as best shown in FIG. 1. The proximal end of each spine puller wire 32 is anchored to the portion of its corresponding slider 58 that is contained within the handle housing 40 by any suitable method. A suitable method for anchoring a spine puller wire 32 to a slider 58 involves a short stainless steel tubing 60 or the like mounted on the proximal end of the puller wire. The slider 58 includes an opening 62 for receiving the stainless steel tubing 60 and a channel 64 distal to the opening having a size that permits a spine puller wire 32 to pass therethrough but that prevents the stainless steel tubing from passing therethrough. Other mechanisms for anchoring the spine puller wires 32 to the sliders 58 are within the scope of the invention.

Other control handles capable of manipulating a plurality of puller wires can also be used in connection with the invention. Examples of such handles are disclosed in U.S. Pat. No. 6,066,125 and U.S. patent application Ser. No. 09/710,210, entitled "Deflectable Catheter with Modifiable Handle," the disclosures of which are incorporated herein by reference.

If desired, each spine 14 can also include one or more location sensors (not shown), such as an electromagnetic location sensor, for conveying locational information about the electrodes on the spine. Use and design of such location sensors are described in more detail in U.S. application Ser. No. 10/040,932, entitled "Catheter Having Multiple Spines Each Having Electrical Mapping and Location Sensing Capabilities," the disclosure of which is incorporated herein by reference.

To use the catheter of the invention, a cardiologist or electrophysiologist introduces a guiding sheath and a dilator into the patient, as is generally known in the art, so that the distal ends of the sheath and dilator are in the region of the heart to be mapped. The dilator is removed from the guiding sheath, and the catheter is introduced into the patient through the guiding sheath. To insert the catheter into the guiding sheath, the mapping assembly 13 must be in its collapsed arrangement, wherein each spine 14 is disposed generally along the longitudinal axis of the catheter body 12. A suitable guiding sheath for use in connection with the catheter is the PREFACE™ Braided Guiding Sheath (commercially available from Biosense Webster, Inc., Diamond Bar, Calif.). Such a guiding sheath has sufficient strength to hold each spine 124 in the collapsed arrangement, such that the spines and also the entire remainder of the catheter can travel within the guiding sheath, from an insertion point in the patient, through a vein or artery and to a desired location in the heart.

Once the distal end of the catheter has reached the desired location, such as a position within the left ventricle of the heart, relative longitudinal movement between the catheter and the guiding sheath is provided to allow at least a portion, and preferably all, of each spine 14 to protrude from the guiding sheath. Preferably the guiding sheath is moved proximally relative to the distal end of the catheter to expose the spines 14. When a spine 14 protrudes from the guiding sheath, the user can then use control handle to manipulate the corresponding spine puller wire 32 to deflect that spine so that it can be positioned in a desired region for mapping. Preferably at least one electrode from each spine 14 is placed into contact with a first plurality of the heart tissue such that electrical, and optionally locational and mechanical, information can be obtained from the contacted heart tissue. The spines 14 can then be further deflected or undeflected and/or repositioned to a second arrangement to contact a second plurality of heart tissue such that electrical, and optionally locational and mechanical, information can be obtained from these tissues as well.

After mapping is completed, the catheter is moved proximally relative to the guiding sheath to retract the spines within the sheath. During mapping, the region between the spines 14 can be prone to thrombus formation, which can make it difficult to withdraw the spines back into the sheath.

To minimize such thrombus formation, irrigation fluid may be introduced through the catheter using an irrigation tube (not shown), as generally described in U.S. patent application Ser. No. 10/040,932, entitled "Catheter Having Multiple Spines Each Having Electrical Mapping and Location Sensing Capabilities."

Using the inventive catheter having multiple spines, each having electrical and optionally mechanical mapping and locational sensing capabilities, the cardiologist can map local activation time and obtain voltage maps. The cardiologist can also determine those locations in the heart having no mechanical activity by monitoring whether the position of the location sensor changes over a complete cardiac cycle. This information can guide the cardiologist in providing therapy to the patient. For example, where the cardiologist finds regions of the heart that do not have mechanical activity, he or she can revascularize those regions using known techniques, such as gene therapy or transmyocardial revasularization. The inventive catheter allows the cardiologist to map the heart more quickly than traditional catheters by measuring multiple points of data at a time.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

What is claimed is:

1. A catheter comprising:
   an elongated catheter body having a proximal end, a distal end and at least one lumen extending longitudinally therethrough;
   a control handle attached to the proximal end of the catheter body;
   a mapping assembly mounted at a junction at the distal end of the catheter body and comprising at least two elongated flexible spines, each spine having a proximal end attached at or near the distal end of the catheter body and a free distal end, wherein each spine carries at least one electrode along its length; and
   at least two spine puller wires, each spine puller wire corresponding to one of the at least two spines, wherein each spine puller wire has a proximal end anchored in the handle and a distal end anchored at or near the distal end of its corresponding spine such that, in use, longitudinal movement of a spine puller wire relative to the catheter body results in deflection of the spine to which the spine puller wire is anchored.

2. The catheter of claim 1, wherein each spine comprises a tip electrode mounted at the distal end of the spine.

3. The catheter of claim 1, wherein each spine comprises an atraumatic tip mounted at the distal end of the spine.

4. The catheter of claim 1, wherein each spine comprises a plastic cap mounted at the distal end of the spine.

5. The catheter of claim 1, wherein each spine further comprises at least one location sensor.

6. The catheter of claim 1, wherein the number of spines ranges from two to twelve.

7. The catheter of claim 1, wherein the number of spines ranges from three to eight.

8. The catheter of claim 1, wherein the catheter further comprises a catheter puller wire having a proximal end anchored in the control handle and a distal end anchored at or near the junction of the mapping assembly and the catheter body such that, in use, longitudinal movement of the catheter puller wire relative to the catheter body results in deflection of the catheter body at or near the junction.

9. The catheter of claim 1, wherein each electrode has a length up to about 2 mm.

10. The catheter of claim 1, wherein each spine carries a plurality of electrodes, and the distance between electrodes on each spine ranges from about 1 mm to about 10 mm.

11. The catheter of claim 10, wherein the distance between electrodes on each spine ranges from about 2 mm to about 5 mm.

12. The catheter of claim 1, wherein each spine carries from 2 to about 20 electrodes.

13. The catheter of claim 1, wherein each spine carries from 3 to 10 electrodes.

* * * * *